United States Patent
Teles et al.

(10) Patent No.: US 7,449,606 B2
(45) Date of Patent: Nov. 11, 2008

(54) METHOD FOR PRODUCING A KETONE

(75) Inventors: Joaquim Henrique Teles, Otterstadt (DE); Beatrice Rößler, Bad Dürkheim (DE); Rolf Pinkos, Bad Dürkheim (DE); Thomas Genger, Lambsheim (DE); Thomas Preiss, Weisenheim am Sand (DE)

(73) Assignee: BASF SE, Ludwigshafen (DE)

( * ) Notice: Subject to any disclaimer, the term of this patent is extended or adjusted under 35 U.S.C. 154(b) by 218 days.

(21) Appl. No.: 10/573,326

(22) PCT Filed: Sep. 23, 2004

(86) PCT No.: PCT/EP2004/010681

§ 371 (c)(1),
(2), (4) Date: Jun. 21, 2006

(87) PCT Pub. No.: WO2005/030690

PCT Pub. Date: Apr. 7, 2005

(65) Prior Publication Data

US 2006/0281952 A1    Dec. 14, 2006

(30) Foreign Application Priority Data

Sep. 25, 2003   (DE) ............................... 103 44 595

(51) Int. Cl.
    *C07C 45/28*   (2006.01)
(52) U.S. Cl. ...................... 568/365; 568/350
(58) Field of Classification Search ................. 568/343, 568/350, 365
    See application file for complete search history.

(56) References Cited

U.S. PATENT DOCUMENTS

| | | | |
|---|---|---|---|
| 2,636,898 | A | 4/1953 | Buckley |
| 3,063,986 | A | 11/1962 | Wesslau et al. |
| 3,656,899 | A | 4/1972 | Baechle et al. |
| 3,804,914 | A | 4/1974 | Fahey |
| B3 16,917 | I5 | 1/1975 | Fahey |
| 4,177,645 | A | 12/1979 | Schwarz et al. |
| 5,128,296 | A | 7/1992 | Matson et al. |
| 5,177,278 | A | 1/1993 | Sanchez |
| 5,180,870 | A | 1/1993 | Paciello |
| 5,210,349 | A | 5/1993 | Matson et al. |
| 5,321,176 | A | 6/1994 | Sanchez |
| 5,849,257 | A | 12/1998 | Fujiwara et al. |
| 6,172,243 | B1 | 1/2001 | Kuroda et al. |

| | | |
|---|---|---|
| 2002/0045791 A1 | 4/2002 | Takahashi et al. |

FOREIGN PATENT DOCUMENTS

| | | |
|---|---|---|
| DE | 2040219 | 3/1971 |
| DE | 25 19 817 | 11/1976 |
| DE | 27 32 267 | 1/1979 |
| EP | 0 285 420 | 10/1988 |
| EP | 1 035 119 | 9/2000 |
| EP | 1 076 217 | 2/2001 |
| EP | 1 170 291 | 1/2002 |
| GB | 649680 | 1/1951 |
| GB | 876531 | 9/1961 |
| GB | 1327401 | 8/1973 |
| GB | 1 551 74 | 8/1979 |
| JP | 2001302570 | 10/2001 |
| JP | 2004059434 | 2/2004 |
| WO | WO-98/25698 | 6/1998 |
| WO | WO-00/73202 | 12/2000 |

OTHER PUBLICATIONS

T. Schiffer, G. Oenbrink, "Cyclododecanol, Cyclododecanon and Laurolactam", Ullmann's Encyclopedia of Industrial Chemistry, 6th Ed., 2000, Electronic Release, Wiley VCH.
G. L. Panov et al., "Non-Catalytic Liquid Phase Oxidation of Alkenes with Nitrous Oxide. 1 Oxidation of Cyclohexene to Cyclohexanone", React. Kinet. Catal. Lett. vol. 76, No. 2 (2002), p. 401-405.
K. A. Dubkov et al., "Non-Catalytic Liquid Phase Oxidation of Alkenes with Nitrous Oxide. 2. Oxidation of Cyclopentene to Cyclopentanone", React. Kinet. Catal. Lett. vol. 77, No. 1 (2002), p. 197-205.
E.V. Starokon et al., "Liquid Phase Oxidation of Alkenes with Nitrous Oxide to Carbonyl Compounds", Adv. Synth. Catal. 2004, 346, p. 268-274.
A. K. Uriarte et al., Nitrous Oxide- Waste to Value, Stud. Surf. Sci. Catal. 130, (2000), p. 743-748.
T. Schiffer et al., "Cyclododecatriene, Cyclooctadiene, and 4-Vinylcyclohexene", Ullmann's Encyclopedia of Industrial Chemistry, 6th Ed. , 2000, Electronic Release, Wiley VCH.
H. Weber et al., "Zur Bildungsweise von cis, trans, trans-Cyclododecatrien (1.5.9) mittels titanhaltiger Katalysatoren", Liebigs Ann. Chem. 681, (1965), p. 10-20.
D. R. Fahey, "Selective Hydrogenation of 1,5,9-Cyclododecatriene to Cyclododecene Catalyzed by Ruthenium Complexes", J. Org. Chem. 38, 1973, p. 80-87.
L.I. Zakharkin et al., "Isomerization of Trans-1,2-Epoxy-Cis, Trans-5,9-Cyclododecadiene, trans-1,2-epoxy-trans,trans-5,9-cyclododecadiene, and trans-epoxycyclododecane to the corresponding ketones by the actio nof lithium and magnesium iodides and bromides", Journal of Organic Chemistry of the USSR, vol. 26, No. 7, p. 1291-1294, 1990.

*Primary Examiner*—Sikarl A Witherspoon
(74) *Attorney, Agent, or Firm*—Connolly Bove Lodge & Hutz LLP

(57) ABSTRACT

A process for preparing a ketone, in particular cyclododecanone, by reacting cyclododecatriene with dinitrogen monoxide to obtain cyclododecadienone and hydrogenating the resulting cyclododecadienone, in particular to give cyclododecanone.

20 Claims, No Drawings

METHOD FOR PRODUCING A KETONE

CROSS REFERENCE TO RELATED APPLICATION

The present application is a National Stage application of PCT/EP 2004/010681, filed Sep. 23, 2004, which claims priority from German Patent Application No. 103 44 595.1, filed Sep. 25, 2003.

The present invention relates to a process for preparing a ketone by oxidizing cyclododecatriene to cyclododecadienone by reacting with dinitrogen monoxide. In a preferred embodiment, the cyclododecadienone is hydrogenated in a further step to cyclododecanone.

Cyclododecanone is an important intermediate for the preparation of, for example, laurolactam, dodecanedicarboxylic acid and polyamides derived therefrom, for example nylon-12 or nylon-6,12.

Cyclododecanone is prepared in the common industrial process by air oxidation of cyclododecane in the presence of boric acid to give cyclododecyl borate, hydrolysis of the borate to give cyclododecanol and subsequent dehydrogenation of the cyclododecanol. Cyclododecane itself is also obtained by fully hydrogenating cyclododecatriene (CDT). One description of this industrial process for synthesizing cyclododecanone can be found in T. Schiffer, G. Oenbrink, "Cyclododecanol, Cyclododecanon and Laurolactam" in Ullmann's Encyclopedia of Industrial Chemistry, 6th Edition, 2000, Electronic Release, Wiley VCH.

However, the industrial process mentioned has a series of disadvantages.

First, the oxidation of cyclododecane with oxygen only ensures acceptable selectivity at low conversions. Even with the addition of boric acid, which protects the cyclododecanol formed from further oxidation in the form of boric ester, the cyclododecane conversion must not be above 30%. After the oxidation, the boric esters have to be hydrolyzed in a separate step, and both the boric acid and the unconverted cyclododecane have to be recycled into the oxidation. Additionally, boron containing waste products are formed, which are difficult to dispose. The main products formed are cyclododecanol and cyclodecanone in a ratio of 10:1.

Secondly, the mixture of cyclododecanol and cyclododecanone which is formed has to be separated by distillation and the cyclododecanol has to be converted to cyclododecanone by dehydrogenation. This dehydrogenation is endothermic and likewise affords only partial conversion. The unconverted cyclododecanol then in turn has to be removed by distillation and recycled into the process.

As a consequence of the incomplete conversion, the conventional process includes several large recycle streams and a series of technically costly and inconvenient distillative separations.

It is an object of the present invention to provide a novel process for preparing cyclododecanone which does not have the disadvantages of the prior art process.

We have found that this object is achieved by a process for preparing cyclododecanone in which cyclododecanone is prepared by hydrogenating cyclododecadienone.

This inventive solution presents the problem of how the cyclododecadienone which is used as the reactant of the hydrogenation can be prepared in a very simple and effective manner.

According to the invention, this problem is solved by a process in which the cyclododecatriene is oxidized to cyclododecadienone by a one-stage reaction with dinitrogen monoxide.

The oxidation of an olefinic compound to an aldehyde or a ketone by means of dinitrogen monoxide is described, for example, in GB 649,680 or in the equivalent U.S. Pat. No. 2,636,898. However, the cyclic olefinic compounds described there are only cyclopentene, cyclohexene, cyclooctene, and cyclooctatetraene. Cyclic compounds having more than 8 carbon atoms or cyclic compounds having 3 C—C double bonds are not described there.

The more recent scientific articles of G. L. Panov et al., "Non-Catalytic Liquid Phase Oxidation of Alkenes with Nitrous Oxide. 1. Oxidation of Cyclohexene to Cyclohexanone", React. Kinet. Catal. Lett. Vol. 76, No. 2 (2002) p. 401-405, and K. A. Dubkov et al., "Non-Catalytic Liquid Phase Oxidation of Alkenes with Nitrous Oxide. 2. Oxidation of Cyclopentene to Cyclopentanone", React. Kinet. Catal. Lett. Vol. 77, No. 1 (2002) p. 197-205 likewise describe oxidations of olefinic compounds with dinitrogen monoxide. However, the disclosures on this subject are restricted exclusively to cyclopentene and cyclohexene.

Also, the scientific article "Liquid Phase Oxidation of Alkenes with Nitrous Oxide to Carbonate Compounds" of E. V. Starokon et al. in "Advanced Synthetic Catalysis" 2004, 346, 268-274 gives a mechanistic study of the oxidation of alkenes with dinitrogen monoxide in the liquid phase.

The preparation of cyclododeca-4,8-dienone from 1,5,9-cyclododecatriene has hitherto only been possible by a two-stage synthesis in which 1,5,9-cyclododecatriene was epoxidized to 1,2-epoxycyclododeca-5,9-diene in a first step and the epoxide was catalytically rearranged in a second step to cyclododeca-4,8-dienone. This process is described, for example, in U.S. Pat. No. 3,063,986. This conventional process has two decisive disadvantages: first, it is difficult to achieve a selective monoepoxidation. Secondly, the process necessarily has two stages.

In comparison, the above-described preferred embodiment of the process according to the invention offers the possibility of starting from 1,5,9-cyclododecatriene to obtain cyclododeca-4,8-dienone in a single step with high selectivity.

The overall process according to the invention for preparing cyclododecanone accordingly comprises two steps, a first step involving the reaction of cyclododecatriene with dinitrogen monoxide to obtain cyclododecadienone and a second step the hydrogenation of cyclododecadienone to obtain cyclododecanone.

Compared to the above-described common process which necessarily comprises the four steps of full hydrogenation of cyclododecatriene to cyclododecane;

air oxidation of the cyclododecane in the presence of boric acid to give cyclododecyl borate;

hydrolysis of the borate to cyclododecanol;

dehydrogenation of the cyclododecanol to obtain cyclododecanone, one feature of the process according to the invention for preparing cyclododecanone is that, starting from the same reactant, cyclododecatriene, the cyclododecanone product can be prepared while saving two reaction stages, thus halving the number of reaction stages.

The present invention accordingly relates to a process for preparing cyclododecanone, comprising the steps (I) and (II)

(I) reacting cyclododecatriene with dinitrogen monoxide to obtain cyclododecadienone;

(II) hydrogenating the cyclododecadienone obtained in (I) to obtain cyclododecanone.

The present invention likewise relates to a process for preparing a ketone by reacting cyclododecatriene with dinitrogen monoxide to obtain cyclododecadienone.

The dinitrogen monoxide used for the reaction may in principle be used in pure form or in the form of a suitable gas mixture comprising dinitrogen monoxide. Moreover, the dinitrogen monoxide may in principle stem from any desired source.

The term "gas mixture" as used in the context of the present invention refers to a mixture of two or more compounds which are in the gaseous state at ambient pressure and ambient temperature. The gas mixture can also have another aggregation with varying temperature or varying pressure, for example a liquid or hypercritic condition, preferably liquid, and is still classified as a gas mixture in the context of the present invention.

When a gas mixture is used, its dinitrogen monoxide content is essentially arbitrary, as long as it is ensured that the reaction according to the invention is possible.

In a preferred embodiment of the process according to the invention, a gas mixture containing at least 10% by volume of dinitrogen monoxide is used, and the dinitrogen monoxide content in the mixtures is preferably in the range from 20 to 99.9% by volume, more preferably in the range from 40 to 99.5% by volume, more preferably in the range from 60 to 99.5% by volume and especially preferably in the range from 80 to 99.5% by volume.

In the context of the present invention the composition of the gas mixtures is given in volume percent. All values given refer to the composition of the gas mixture at ambient pressure and ambient temperature.

Accordingly, the present invention also relates to a process as described above, wherein cyclododecatriene is reacted with a gas mixture containing from 20 to 99.9% by weight of dinitrogen monoxide, based on the total weight of the gas mixture.

The term "gas mixture" as used in the context of the present invention also refers to mixtures which, in addition to dinitrogen monoxide, contain at least one further component, preferably one further gas. The component can also be a gas which is for example liquid under the conditions chosen. In this context, essentially all gases are conceivable, as long as it is ensured that the reaction of cyclododecatriene with dinitrogen monoxide is possible. Preference is accordingly given in particular to gas mixtures which, in addition to dinitrogen monoxide, contain at least one inert gas. The term "inert gas" as used in the context of the present invention refers to a gas which behaves inertly with regard to the reaction of dinitrogen monoxide with cyclododecatriene. Useful inert gases are, for example, nitrogen, carbon dioxide, carbon monoxide, hydrogen, water, argon, methane, ethane and propane.

Equally, the gas mixture may also contain components, preferably gases which do not behave as inert components, preferably as inert gases in the reaction of $N_2O$ with cyclododecatriene. Useful such gases include $NO_x$ or, for example, oxygen. The term "$NO_x$," as used in the context of the present invention, relates to all compounds $N_aO_b$ except dinitrogen monoxide, wherein a is 1 or 2 and b is a number from 1 to 6. Instead of the term "$NO_x$," the term "nitrogen oxides" is also used in the context of the present invention. In such a case, preference is given to using those gas mixtures whose content of these gases is in the range from 0 to 0.5% by volume, based on the total volume of the gas mixture.

Accordingly, the present invention also describes a process as described above, wherein the gas mixture contains from 0 to 0.5% by volume of oxygen or from 0 to 0.5% by volume of nitrogen oxides or both from 0 to 0.5% by volume of oxygen and from 0 to 0.5% by volume of nitrogen oxides, based in each case on the total volume of the gas mixture. In this context, a value of, for example, 0.5% by volume relates to a total content of all possible nitrogen oxides apart from dinitrogen monoxide of 0.5% by volume.

In principle, the composition of the gas mixture can be determined for every method known to the person skilled in the art in the context of the present invention. In the context of the present invention, the composition of the gas mixtures is preferably determined by gas chromatography. It can also be determined by UV-spectroscopy, IR-spectroscopy or by chemical methods.

According to the present invention, dinitrogen monoxide or the gas mixture containing dinitrogen monoxide can be used in every form, in particular as a gas or in liquid form. Dinitrogen monoxide or the gas mixture containing dinitrogen monoxide can be liquidified by all methods known to the person skilled in the art, preferably by choosing a suitable pressure and a suitable temperature.

According to the present invention, it is also possible that dinitrogen monoxide or the gas mixture containing dinitrogen monoxide is first absorbed in a suitable solvent and then added to the reaction.

In a preferred embodiment of the present invention, the dinitrogen monoxide source is at least one dinitrogen monoxide-containing offgas of a chemical process. The scope of the present invention also includes embodiments in which the dinitrogen monoxide source used is at least two nitrogen monoxide-containing offgases of a single plant. Likewise included are embodiments in which the dinitrogen monoxide source used is at least one dinitrogen monoxide-containing offgas of one plant and at least one further dinitrogen monoxide-containing offgas of at least one further plant.

The present invention accordingly also relates to a process as described above, wherein the dinitrogen monoxide source used is at least one dinitrogen monoxide-containing offgas of at least one industrial process.

In the context of the present invention, it is also possible that dinitrogen monoxide used in the process according to the invention is prepared for the process. Preference is given to the preparation by thermal decomposition of $NH_4NO_3$ as disclosed, for example, in U.S. Pat. No. 3,656,899 whose contents on this subject is fully incorporated by reference into the context of the present application. Likewise preferred is a preparation by catalytic oxidation of ammonia, as disclosed for example in U.S. Pat. No. 5,849,257 or in WO 98/25698, whose contents on this subject are fully incorporated by reference into the context of the present application.

In the context of the present invention, the term "dinitrogen monoxide source" relates both to embodiments in which the offgas mentioned is used in unmodified form in the inventive conversion of cyclododecatriene, and embodiments in which at least one of the offgases mentioned is subjected to a modification.

The term "modification" as used in this context within the scope of the present invention relates to any suitable process by which the chemical composition of an offgas is changed. Accordingly, the term "modification" relates, among other embodiments, to those in which a dinitrogen monoxide-containing offgas is concentrated with respect to the dinitrogen monoxide content in at least one suitable process. Such processes are described, for example, in DE-A 27 32 267, EP 1 076 217 A2 or WO 00/73202 A1, whose contents on this subject are fully incorporated by reference into the context of the present application.

In the context of the present invention, the gas mixture can also be the subject of a modification to reduce the concentration of inert or non-inert compounds in the gas mixture.

According to the present invention, this modification can for example be an absorption of the gas mixture in a suitable solvent and subsequent desorption to purify the gas mixture from inert components. A suitable solvent for the absorption is, for example, water, as disclosed in DT 20 40 219.

According to the present invention, the modification of the gas mixture can also comprise a further purification step, for example a step for separating of $NO_x$ from the gas mixture. Suitable processes for separating of $NO_x$ are in principle known from the state of the art. According to the present invention, all processes for separating of $NO_x$ known to the person skilled in the art can be used.

According to the invention, it is preferred that the offgases are subjected to treatment comprising the absorption in a suitable solvent and subsequent desorption to remove inert compounds. A suitable solvent is, for example, water, as disclosed in DT 20 40 219.

In an example of a preferred embodiment of the process according to the invention, it is possible to concentrate the abovementioned dinitrogen monoxide-containing offgas by feeding it to at least one adsorption column and dissolving the dinitrogen monoxide in at least one organic solvent. An example of suitable solvent for this purpose is cyclododecatriene. This inventive process variant offers the advantage that the resulting solution of dinitrogen monoxide in cyclododecatriene can be fed without further workup to the conversion according to the invention. This solution of dinitrogen monoxide in cyclododecatriene may contain dinitrogen monoxide in all conceivable concentrations up to saturation. In other embodiments, at least one further solvent or a mixture of cyclododecatriene and at least one further solvent may be used for adsorption. Such further solvents are, for example, all suitable common organic solvents. Preferred solvents include N-methylpyrrolidone, dimethylformamide, dimethyl sulfoxide, propylene carbonate, sulfolane and N,N-dimethylacetamide. When at least one further solvent or a mixture of cyclododecatriene and at least one further solvent is used, a further preferred embodiment involves at least partly, preferably substantially fully, obtaining the dinitrogen monoxide from the solution enriched with dinitrogen monoxide in at least one suitable desorption step, and feeding it to the conversion according to the invention.

In a further embodiment, the chemical composition of an offgas may also be changed by adding pure dinitrogen monoxide to the offgas.

In a further preferred embodiment of the present invention, the at least one dinitrogen monoxide-containing offgas stems from an adipic acid plant, a dodecanedioic acid plant, a hydroxylamine plant and/or a nitric acid plant, in which case the latter is in turn preferably operated with an offgas of an adipic acid plant, of a dodecanedioic acid plant or of a hydroxylamine plant.

In a preferred embodiment, the offgas stream used is from an adipic acid plant in which oxidation of cyclohexanol/cyclohexanone mixtures with nitric acid generally forms from 0.8 to 1.0 mol of $N_2O$ per mole of adipic acid formed. As described, for example, in A. K. Uriarte et al., Stud. Surf. Sci. Catal. 130 (2000) p. 743-748, the offgases of adipic acid plants also contain, in varying concentrations, further constituents including nitrogen, oxygen, carbon dioxide, carbon monoxide, nitrogen oxides, water and volatile organic compounds.

The abovementioned dodecanedioic acid plant is a substantially identical type of plant.

An example of a typical composition of an offgas of an adipic acid plant or of a dodecanedioic acid plant is reproduced in the following table:

| Component | Concentrations/% by weight |
|---|---|
| $NO_x$ | 19-25 |
| $N_2O$ | 20-28 |
| $N_2$ | 30-40 |
| $O_2$ | 7-10 |
| $CO_2$ | 2-3 |
| $H_2O$ | ~7 |

The offgas stream of an adipic acid plant or of a dodecanedioic acid plant may be used directly in the process according to the invention. Preference is given to cleaning the offgas stream of the adipic acid plant or of a dodecanedioic acid plant before use for converting the cyclododecatriene. For example, it is advantageous to adjust the oxygen and/or nitrogen oxides content of the offgas stream to contents in the range of each from 0 to 0.5% by volume. The above-cited document of A. K. Uriarte et al. discloses various possibilities of how such an offgas stream can be cleaned for use in catalytic benzene hydroxylation. The document describes absorption processes, for example pressure swing absorption, membrane separation processes, low temperature distillation or a combination of selective catalytic reduction with ammonia followed by catalytic removal of oxygen. All of these cleaning methods can also be applied in order to clean the dinitrogen monoxide-containing offgas stream of an industrial plant, for example of an adipic acid plant or of a dodecanedioic acid plant or of a nitric acid plant. Very particular preference is given to the distillative cleaning and therefore distillative concentration of the offgas stream of an adipic acid plant or of a dodecanedioic acid plant or of a nitric acid plant.

Particular preference is given in the context of the present invention to purifying the offgas stream of an adipic acid plant or of a dodecanedioic acid plant in the case that it contains in each case more than 0.5% by volume of oxygen and/or nitrogen oxides.

Accordingly, the present invention also describes a process as described above, wherein the cyclododecatriene is converted using the offgas stream of an adipic acid plant or of a dodecanedioic acid plant.

Accordingly, the present invention further describes a process as described above, wherein the offgas stream, which has preferably been distillatively cleaned if necessary, of the adipic acid plant or of a dodecanedioic acid plant contains oxygen and/or nitrogen oxides in the range of in each case from 0 to 0.5% by volume.

In a likewise preferred embodiment, the offgas stream used is of a nitric acid plant which is supplied, entirely or partly, with offgases comprising dinitrogen monoxide and nitrogen oxides from other processes. In such nitric acid plants, nitrogen oxides are adsorbed and converted for the most part to nitric acid, whereas the dinitrogen monoxide is not converted. For example, such a nitric acid plant may be supplied with nitrogen oxides which are prepared by selective combustion of ammonia, and with offgases of an adipic acid plant and/or with offgases of a dodecanedioic acid plant. It is equally possible to supply such a nitric acid plant solely with offgases of an adipic acid plant and/or with offgases of a dodecanedioic acid plant.

The offgases of such nitric acid plants always contain different concentrations of further constituents including nitrogen, oxygen, carbon dioxide, carbon monoxide, nitrogen oxides, water and volatile organic compounds.

An example of a typical composition of an offgas of such a nitric acid plant is reproduced in the table which follows:

| Component | Concentrations/% by wt. |
|---|---|
| $NO_x$ | <0.1 |
| $N_2O$ | 8-36 |
| $N_2$ | 57-86 |
| $O_2$ | 3-9 |
| $CO_2$ | 1-4 |
| $H_2O$ | ~0.6 |

The offgas stream of a nitric acid plant may be used directly in the process according to the invention. Preference is given to purifying the offgas stream of the nitric acid plant before using it to convert the cyclododecatriene. For example, it is advantageous to adjust the content of oxygen and/or nitrogen oxides in the offgas stream to contents in the range of in each case from 0 to 0.5% by volume. Suitable processes by which these values can be attained are described above in the context of the adipic acid plant and dodecanedioic acid plant. Very particular preference is also given in the context of the off-gases of the nitric acid plant to distillative purification and therefore to distillative concentration.

Particular preference is given in the context of the present invention to purifying the offgas stream of a nitric acid plant in the case that it contains in each case more than 0.5% by volume of oxygen and/or nitrogen oxides.

The present invention accordingly also relates to a process as described above, wherein the cyclododecatriene is converted using the dinitrogen monoxide-containing offgas stream of a nitric acid plant.

The present invention accordingly further relates to a process as described above, wherein the offgas stream of the nitric acid plant, which has preferably been purified by distillation if necessary, contains oxygen and/or nitrogen oxides in a range from 0 to 0.5% by volume.

In a likewise preferred embodiment of the process according to the invention, the offgas stream of a hydroxylamine plant is used, in which, for example, ammonia is initially oxidized with air or oxygen to NO and small amounts of dinitrogen monoxide are by-produced. The NO is subsequently hydrogenated with hydrogen to give hydroxylamine. Since dinitrogen monoxide is inert under the hydrogenation conditions, it accumulates in the hydrogen circuit. In preferred process versions, the purge stream of a hydroxylamine plant contains dinitrogen monoxide in the range from 9 to 13% by volume in hydrogen. This purge stream may be used as such for the conversion according to the invention. It is equally possible to suitably concentrate this stream with respect to the dinitrogen monoxide content as described above.

The present invention accordingly also relates to a process as described above, wherein the dinitrogen monoxide source is the offgas of an adipic acid plant and/or of a dodecanedioic acid plant and/or of a hydroxylamine plant and/or of a nitric acid plant operated with the offgas of an adipic acid plant and/or of a dodecanedioic acid plant and/or of a hydroxylamine plant.

The present invention likewise relates to an integrated process for preparing cyclododeca-4,8-dienone, which comprises at least the following steps (i) and (ii):
(i) providing a dinitrogen monoxide-containing gas mixture containing in each case from 0 to 0.5% by volume of oxygen and/or nitrogen oxides and based on at least one offgas stream of at least one adipic acid plant and/or of at least one dodecanedioic acid plant and/or of at least one hydroxylamine plant and/or of at least one nitric acid plant operated with the offgas of an adipic acid plant and/or of a dodecanedioic acid plant and/or of a hydroxylamine plant;
(ii) reacting cyclododecatriene with the gas mixture provided in (i) to obtain cyclododeca-4,8-dienone.

It is equally possible in the context of the process according to the invention to selectively prepare dinitrogen monoxide for use in the process. Preference is given, inter alia, to the preparation via the thermal decomposition of $NH_4NO_3$, as described, for example, in U.S. Pat. No. 3,656,899, whose contents on this subject are fully incorporated by reference into the context of the present application. Preference is likewise also given to the preparation via the catalytic oxidation of ammonia, as described, for example, in U.S. Pat. No. 5,849,257 or in WO 98/25698, whose contents on this subject are fully incorporated by reference into the context of the present application.

In the inventive reaction of cyclododecatriene with dinitrogen monoxide, at least one suitable solvent or diluent may be used. These include cyclododecane or cyclododecanone or saturated aliphatic or aromatic, unsubstituted or alkyl-substituted hydrocarbons, although substantially all common solvents and/or diluents are suitable, with the proviso that they have neither a C—C double bond nor a C—C triple bond nor an aldehyde group.

In general, it is not necessary to add a solvent or diluent in the inventive reaction with dinitrogen monoxide.

There are generally no particular restrictions with regard to the reaction conditions of the conversion of cyclododecatriene, as long as it is ensured that cyclododeca-4,8-dienone is obtained from the reaction.

The temperatures in the reaction of cyclododecatriene with dinitrogen monoxide are preferably in the range from 140 to 350° C., more preferably in the range from 160 to 275° C. or in the range from 200 to 310 ° C. and particularly preferably in the range from 180 to 250° C. or in the range from 250 to 300 ° C.

It is possible in the process according to the invention to carry out the reaction at two or more temperatures, i.e. in two or more temperature ranges which are each within the abovementioned limits. Temperature changes in the course of the reaction may be implemented continuously or else discontinuously.

The pressures in the reaction of cyclododecatriene-with dinitrogen monoxide are preferably higher than the autogenous pressure of the reactant or product mixture at the selected reaction temperature or the selected reaction temperatures. The pressures are preferably in the range from 1 to 1000 bar, more preferably in the range from 40 to 300 bar and particularly preferably in the range from 50 to 200 bar.

It is possible in the process according to the invention to carry out the reaction at two or more pressures, i.e. in two or more pressure ranges which are each within the abovementioned limits. Pressure changes in the course of the reaction can be implemented continuously or else discontinuously.

Accordingly, the present invention also relates to a process as described above, wherein the reaction in (ii) is carried out at a temperature in the range from 140 to 350° C. and a pressure in the range from 1 to 1000 bar.

With regard to the reactors which can be used for the conversion, there are no particular restrictions. In particular, the conversion may be in batch mode or in continuous mode. Accordingly, the reactors used may be, for example, at least one CSTR (continuous stirred tank reactor) having at least one internal and/or at least one external heat exchanger, at least one tubular reactor or at least one loop reactor. It is equally possible to configure at least one of these reactors in such a way that it has at least two different zones. Such zones may differ, for example, in reaction conditions, for example the temperature or the pressure and/or in the geometry of the zone, for example the volume or the cross section. When the reaction is carried out in two or more reactors, two or more of the same reactor types or at least two different reactor types may be used.

In a preferred embodiment, the inventive reaction with dinitrogen monoxide is carried out in a single reactor. Preference is given, for example, to the reaction in continuous mode.

The residence time of the reactants in the at least one reactor is generally in the range of up to 20 h, preferably in the range from 0.1 to 20 hours, more preferably in the range from 0.2 to 15 hours and particularly preferably in the range from 0.25 to 10 h.

In the feed which is fed to the reaction of dinitrogen monoxide with cyclododecatriene, the molar ratio of dinitrogen monoxide to cyclododecatriene is generally in the range from 0.05 to 4, preferably in the range from 0.06 to 1, more preferably in the range from 0.07 to 5 and in particular from 0.1 to 0.4. According to an alternative embodiment of the present invention, preferred ranges are in the range from 0.2 to 4, preferably in the range from 0.3 to 3, more preferably in the range from 0.4 to 2 and particularly preferably in the range from 0.4 to 1.5.

In a particularly preferred embodiment, the process according to the invention is carried out in such a way that a conversion of cyclododecatriene in the range of up to 95%, preferably in the range from 1 to 80%, more preferably in the range from 5 to 50%, especially preferably in the range from 8 to 25%. According to an alternative embodiment, preferred ranges are from 10 to 80%, more preferably in the range from 21 to 75% and especially preferably in the range from 20 to 50% is achieved at a very high selectivity with respect to cyclododecadienone. The selectivity based on cyclododecadienone is generally at least 90%, preferably at least 92.5% and more preferably at least 95%.

The present invention accordingly also relates to a process as described above, wherein the reaction of dinitrogen monoxide with cyclododecatriene has a conversion of cyclododecatriene in the range from 1 to 80%, preferably in the range from 5 to 30% at a selectivity based on cyclododecadienone of at least 90%.

In the context of the present invention, in principle any cyclododecatriene or any mixture of two or more different cyclododecatrienes with dinitrogen monoxide may be converted. These include, for example, 1,5,9-cyclododecatrienes, for example cis,trans,trans-1,5,9-cyclododecatriene or cis,cis,trans-1,5,9-cyclododecatriene or all-trans-1,5,9-cyclododecatriene.

In a very particularly preferred embodiment of the process according to the invention, the cyclododecatriene used is cis,trans,trans-1,5,9-cyclododecatriene.

The present invention accordingly also relates to a process as described above, wherein the cyclododecatriene used is cis,trans,trans-1,5,9-cyclododecatriene.

In particular, the present invention therefore also relates to a process as described above, wherein cis,trans,trans-1,5,9-cyclododecatriene is reacted with dinitrogen monoxide to give cyclododeca-4,8-dienone.

The inventive reaction of cis,trans,trans-1,5,9-cyclododecatriene with dinitrogen monoxide generally results in a cyclododeca-4,8-dienone isomer mixture which comprises at least two of the cis,trans-cyclododeca-4,8-dienone, trans,cis-cyclododeca-4,8-dienone and trans,trans-cyclododeca-4,8-dienone isomers. Preference is given in accordance with the invention for obtaining an isomer mixture in which trans,cis isomer and cis,trans isomer are formed in about the same amounts and the trans,trans isomer is formed only in small amounts compared to the two other isomers. An example of a typical isomer mixture accordingly has the isomers in molar ratios of about 1:1:0.08.

The inventive conversion of at least one cyclododecatriene, preferably the conversion of at least one 1,5,9-cyclododecatriene and especially preferably the conversion of cis,trans,trans-1,5,9-cyclododecatriene may in principle be effected in the presence of a catalyst. In a preferred embodiment of the process according to the invention, the reaction with dinitrogen monoxide is carried out without the addition of a catalyst.

The present invention accordingly also describes a process as described above, wherein the reaction of cyclododecatriene with dinitrogen monoxide is carried out without the addition of a catalyst.

In general, it is not necessary to add a solvent or diluent in the inventive reaction with dinitrogen monoxide.

The 1,5,9-cyclododecatriene which is used with preference may be prepared, for example, by trimerizing pure 1,3-butadiene, as described, for example, in T. Schiffer, G. Oenbrink, "Cyclodecatriene, Cyclooctadiene, and 4-Vinylcyclohexene", Ulmann's Encyclopedia of Industrial Chemistry, 6th Edition (2000), Electronic Release, Wiley VCH. In the case of trimerization in the presence of Ziegler catalysts, this process results, for example, in cis,trans,trans-1,5,9-cyclododecatriene, cis,cis,trans-1,5,9-cyclododecatriene and all-trans-1,5,9-cyclododecatriene, as described, for example, in H. Weber et al. "Zur Bildungsweise von cis,trans,trans-Cyclododecatrien-(1.5.9) mittels titanhaltiger Katalysatoren" in: Liebigs Ann. Chem. 681 (1965) p.10-20. While all of these cyclododecatrienes may be oxidized by means of dinitrogen monoxide, individually or as a mixture of two or more thereof, in the process according to the invention, particular preference is given in the present process according to the invention, as described above, to converting cis,trans,trans-1,5,9-cyclododecatriene. This cis,trans,trans-1,5,9-cyclododecatriene is more preferably prepared in accordance with the abovementioned article by Weber et al., whose contents on this subject are fully incorporated by reference into the context of the present application.

The present invention accordingly also relates to a process as described above, wherein the cyclododecatriene used as a reactant is prepared by trimerizing 1,3-butadiene using a titanium catalyst.

While all suitable titanium catalysts may in principle be used for trimerization, particular preference is given to the titanium tetrachloride/ethylaluminum sesquichloride catalyst described in the article by Weber et al.

The butadiene used for the trimerization especially preferably has a degree of purity determined by gas chromatography of at least 99.6% and more preferably of at least 99.65%. Especially preferably, the 1,3-butadiene used, within the precision of detection, contains no 1,2-butadiene and no 2-butyne.

This preferred trimerization generally results in mixtures which contain at least 95% by weight, preferably at least 96% by weight and more preferably at least 97% by weight, of cis,trans,trans-1,5,9-cyclododecatriene. For example, the mixtures especially preferably contain about 98% by weight of cis,trans,trans-1,5,9-cyclododecatriene.

This cis,trans,trans-1,5,9-cyclododecatriene-containing mixture may be used as such for the reaction with dinitrogen monoxide. It is equally possible to remove the cis,trans,trans-1,5,9-cyclododecatriene from the mixture by at least one suitable method, for example and with preference by at least one distillation, and use it in the reaction with dinitrogen monoxide. There is preferably no such purification in the process according to the invention.

With regard to further details on the trimerization, reference is made to the article by Weber et al.

The inventive reaction of cyclododecatriene with dinitrogen monoxide generally results in a mixture which comprises cyclododecadienone, preferably cyclododeca-4,8-dienone, and in some cases unconverted reactant and/or in some cases at least one by-product. Depending on the further utilization and/or workup, the cyclododecadienone, preferably the cyclododeca4,8-dienone, may be removed from this mixture. In the case that the mixture comprises cyclododecadienone and, for example, a diketone such as cyclododecenedione, it is possible to remove the cyclododecadienone, preferably the cyclododeca4,8-dienone, in a simple manner, and feed it to a further process step, for example the partial hydrogenation to cyclododecenone or preferably to the hydrogenation to cyclododecanone.

It is possible to remove the cyclododeca-4,8-dienone from this mixture by at least one suitable method. Preference is given in this context to distillative removal. The distillation is effected at a pressure in the range of generally from 0.001 to 2 bar, preferably in the range from 0.01 to 1 bar and especially preferably in the range from 0.03 to 0.5 bar, for example from 0.04 to 0.5 bar or 0.05 to 0.5 bar.

The cyclododecadienone obtained in accordance with the invention from the reaction of cyclododecatriene with dinitrogen monoxide may be fed to one or more of any further processes. For example, the keto group of cyclododecadienone may be subjected to a chemical reaction. Equally, at least one of the C—C double bonds may be subjected to a chemical reaction. For example and with preference, at least one C—C double bond, preferably both C—C double bonds, may be hydrogenated.

Irrespective of which regioisomer of cyclododecadienone or which mixture of at least two regioisomeric cyclododecadienones is obtained from the inventive reaction with dinitrogen monoxide, this regioisomer or this regioisomer mixture is preferably hydrogenated to cyclododecanone.

In a preferred embodiment of the process according to the invention, cyclododeca-4,8-dienone is hydrogenated to cyclododecanone.

The present invention accordingly also relates to a process as described above, wherein the cyclododecadienone obtained from the reaction of cyclododecatriene with dinitrogen monoxide is hydrogenated to obtain cyclododecanone.

For the hydrogenation of cyclododecadienone and especially preferably cyclododeca-4,8-dienone, all suitable catalysts may be used. In particular, at least one homogeneous or at least one heterogeneous or both at least one homogeneous and at least one heterogeneous catalyst can be used.

The catalysts which can be used preferably contain at least one metal from the $7^{th}$, the $8^{th}$, the $9^{th}$, the $10^{th}$ or the $11^{th}$ transition group of the Periodic Table of the Elements. Preference is further given to the catalysts which can be used in accordance with the invention containing at least one element selected from the group consisting of Re, Fe, Ru, Co, Rh, Ir, Ni, Pd, Pt, Cu and Au. Particular preference is given to the catalysts which can be used in accordance with the invention containing at least one element selected from the group consisting of Fe, Ni, Pd, Pt and Cu. Especially preferably, the catalyst used according to the present invention contains Pd.

Homogeneous catalysts used with preference in the process according to the invention preferably contain at least one element of the $8^{th}$, $9^{th}$ or $10^{th}$ transition group. Preference is further given to homogeneous catalysts which contain Ru, Rh, Ir and/or Ni. Examples include $RhCl(TTP)_3$ or $Ru_4H_4(CO)_{12}$. Particular preference is given to those homogeneous catalysts which contain Ru. For example, homogeneous catalysts are used as described in U.S. Pat. Nos. 5,180,870, 5,321,176, 5,177,278, 3,804,914, 5,210,349, 5,128,296, U.S. B 316,917 and in D. R. Fahey in J. Org. Chem. 38 (1973) p. 80-87, whose disclosure content on this subject is fully incorporated by reference into the context of the present application. Such catalysts are, for instance, $(TPP)_2(CO)_3Ru$, $[Ru(CO)_4]_3$, $(TPP)_2Ru(CO)_2Cl_2$, $(TPP)_3(CO)RuH_2$, $(TPP)_2(CO)_2RuH_2$, $(TPP)_2(CO)_2RuClH$ or $(TPP)_3(CO)RuCl_2$.

Particular preference is given in the process according to the invention to using at least one heterogeneous catalyst, in which case at least one of the abovementioned metals may be used as the metal as such, as a Raney catalyst and/or applied to a customary support.

Preferred support materials are, for instance, activated carbons or oxides, for example aluminum oxides, silicon oxides, titanium oxides or zirconium oxides. Support materials likewise include bentonites. When two or more metals are used, these may be separate or an alloy. It is possible in this context to use at least one other metal as such and at least one other metal as a Raney catalyst or at least one metal as such and at least one other metal applied to at least one support or at least one metal as the Raney catalyst and at least one other metal applied to at least one support or at least one metal as such and at least one other metal as the Raney catalyst and at least one other metal applied to at least one support.

The catalysts used in the process according to the invention may also be, for example, precipitation catalysts. Such catalysts may be prepared by precipitating their catalytically active components from their salt solutions, in particular from the solutions of their nitrates and/or acetates, for example by adding solutions of alkali metal and/or alkaline earth metal hydroxide and/or carbonate solutions, for example sparingly soluble hydroxides, oxide hydrates, basic salts or carbonates, subsequently drying the resulting precipitates and then converting them by calcining at generally from 300 to 700° C., in particular from 400 to 600° C., to the corresponding oxides, mixed oxides and/or mixed-valence oxides, which are reduced by treatment with hydrogen or hydrogen-containing gases in the range of generally from 50-700° C., in particular from 100 to 400° C., to the metals in question and/or oxidic compounds of lower oxidation state and converted to the actual catalytically active form. Reduction is generally effected until no more water is formed. In the preparation of precipitation catalysts which contain a support material, the catalytically active components may be precipitated in the presence of the support material in question. The catalytically active components may advantageously be precipitated from the salt solutions in question at the same time as the support material.

Preference is given to using hydrogenation catalysts in the process according to the invention which contain the metals or metal compounds catalyzing the hydrogenation deposited on a support material.

Apart from the abovementioned precipitation catalysts which, apart from the catalytically active components, additionally also contain a support material, suitable support materials for the process according to the invention are generally those in which the catalytically hydrogenating component has been applied to a support material, for example by impregnation.

The way in which the catalytically active metal is applied to the support is generally not critical and may be brought about in various ways. The catalytically active metals may be applied to these support materials, for example by saturation with solutions or suspensions of the salts or oxides of the elements in question, drying and subsequent reduction of the metal compounds to give the metals in question or compounds of lower oxidation state by means of a reducing agent, preferably with hydrogen or complex hydrides. Another means of applying the catalytically active metals to these supports is to impregnate the supports with solutions of salts which readily decompose thermally, for example with nitrates or complexes which readily decompose thermally, for example carbonyl or hydrido complexes of the catalytically active metals, and to heat the support saturated in this way to temperatures in the range from 300 to 600° C. to thermally decompose the adsorbed metal compounds. This thermal decomposition is preferably carried out under a protective gas atmosphere. Suitable protective gases are, for example, nitrogen, carbon dioxide, hydrogen or noble gases. In addition, catalytically active metals may be deposited on the catalyst support by vapor deposition or by flame spraying. The catalytically active metals content of these supported catalysts is in principle not critical for the success of the process according to the invention. In general, higher catalytically active metals contents of these supported catalysts lead to higher space-time conversions than lower contents. In general, supported catalysts are used whose catalytically active metals content is in the range from 0.1 to 90% by weight, preferably in the range from 0.5 to 40% by weight, based on the total weight of the catalyst. Since these contents specifications relate to the entire catalyst including support material, but the different support materials have very different specific weights and specific surface areas, it is also conceivable that these data may also be lower or higher than the specifications without this having a disadvantageous effect on the result of the process according to the invention. It will be appreciated that a plurality of catalytically active metals may also be applied to the particular support material. In addition, the catalytically active metals may be applied to the support, for example, by the process of DE-A 25 19 817 or EP 0 285 420 A1. In the catalysts according to the abovementioned documents, the catalytically active metals are an alloy which are generated by thermally treating and/or reducing the, for example, by impregnating with a salt or complex of the aforementioned metals.

Both the precipitation catalysts and the supported catalysts may be activated in situ at the beginning of the reaction by the hydrogen present. Preference is given to separately activating these catalysts before their use.

Useful support materials are generally the oxides of aluminum and titanium, zirconium dioxide, silicon dioxide, clay earths, for example montmorillonites, silicates, for example magnesium or aluminum silicates, zeolites, for example the ZSM-5 or ZSM-10 structure types, or activated carbon. Preferred support materials are aluminum oxides, titanium dioxides, silicon dioxide, zirconium dioxide and activated carbon. It will be appreciated that mixtures of different support materials may also serve as the support for catalysts which can be used in the process according to the invention.

The at least one heterogeneous catalyst may be used, for example, as a suspension catalyst and/or as a fixed bed catalyst.

When the hydrogenation in the process according to the invention is carried out, for example, with at least one suspension catalyst, preference is given to hydrogenating in at least one tubular reactor or in at least one bubble column or in at least one packed bubble column or in a combination of two or more identical or different reactors.

The term "different reactors" in the present context refers either to different reactor types or to reactors of the same type which differ, for example, by their geometry, for example their volume and/or their cross section and/or by the hydrogenation conditions in the reactors.

When, for example, the hydrogenation in the process according to the invention is carried out with at least one fixed bed catalyst, preference is given to using at least one tubular reactor, for example at least one shaft reactor and/or at least one tube bundle reactor, in which case a single reactor can be operated in liquid phase or trickle mode. When two or more reactors are used, at least one may be operated in liquid phase mode and at least one in trickle mode.

In a preferred embodiment of the process according to the invention, the at least one catalyst used for the hydrogenation is removed from the product mixture of the hydrogenation. Depending on the catalyst used, this removal may be effected by any suitable process.

When the catalyst used in the hydrogenation is, for example, a heterogeneous catalyst as a suspension catalyst, preference is given to removing it in the present invention by at least one filtration step. The catalyst removed in this way may be recycled into the hydrogenation or fed to at least one of any other processes. It is equally possible to work up the catalyst, for example in order to recover metal present in the catalyst.

When the catalyst used in the hydrogenation is, for example, a homogeneous catalyst, preference is given to removing it by at least one distillation step in the process according to the invention. In the course of this distillation, one or two or more distillation columns may be used. The catalyst removed in this way may be recycled into the hydrogenation or fed to at least one of any other processes. It is equally possible to work up the catalyst, for example in order to recover metal present in the catalyst.

Before use in any process, for example recycling into the process according to the invention, either the at least one homogeneous or the at least one heterogeneous catalyst, should this be necessary, are regenerated by at least one suitable process.

Heat may be removed from the reactor used in accordance with the invention internally, for example using cooling coils, and/or externally, for example using at least one heat exchanger. When, for example and with preference, at least one tubular reactor is used for hydrogenating, preference is given to conducting the reaction via external circulation in which the removal of heat is integrated.

When, in a preferred embodiment of the process according to the invention, the hydrogenation is carried out continuously, preference is further given to using at least two reactors, more preferably at least two tubular reactors, more preferably at least two tubular reactors connected in series and especially preferably two tubular reactors connected in series. The hydrogenation conditions in the reactors used may in each case be the same or different and are each within the above-described ranges.

When the hydrogenation is carried out over at least one suspended catalyst, the residence time is generally in the range from 0.5 to 50 h, preferably in the range from 1 to 30 h and more preferably in the range from 1.5 to 25 h. It is unimportant in accordance with the invention whether one reactor or at least 2 reactors connected in series are used. For all of these embodiments, the total residence time is within the above-specified ranges.

When in the process according to the invention, the hydrogenation is carried out in continuous mode over at least one fixed bed catalyst, the residence time is generally in the range from 0.1 to 20 h, preferably in the range from 0.2 to 15 h and more preferably in the range from 0.3 to 10 h. It is unimportant in accordance with the invention whether one reactor or at least 2 reactors connected in series are used. For all of these embodiments, the total residence time is within the above-specified ranges.

The mixture which is obtained from the first tubular reactor contains cyclododecanone in a proportion, based on the total content of $C_{12}$ components in the mixture, which is preferably in the range from 50 to 99.9% by weight and more preferably in the range from 70 to 99.5% by weight. This mixture is, optionally after at least one suitable intermediate treatment, fed to the second tubular reactor. The mixture which is obtained from the second tubular reactor contains cyclododecanone in a proportion which is preferably in the range of at least 99.5%, especially in the range of 99.9% and especially preferably of 99.99% by weight, more preferably in the range of at least 99.9% and especially preferably of at least 99.99% by weight.

The hydrogen pressure in the hydrogenation according to the invention is generally in the range from 1 to 325 bar, preferably in the range from 1.5 to 200 bar, more preferably in the range from 2 to 100 bar and especially preferably in the range from 2.5 to 50 bar. The hydrogenation temperature is generally in the range from 0 to 250° C., preferably in the range from 20 to 200° C., for example in the range from 30 to 180° C., more preferably in the range from 30 to 150° C., more preferably in the range from 40 to 170 and especially preferably in the range from 40 to 140° C.

The present invention accordingly also relates to a process as described above, wherein the hydrogenation is carried out in the presence of a hydrogenation catalyst, preferably of a heterogeneous hydrogenation catalyst, at a temperature in the range from 0 to 250° C. and a pressure in the range from 1 to 325 bar.

In the hydrogenation according to the invention, at least one suitable solvent or diluent may be used. Useful solvents and diluents include cyclododecanone or cyclododecane and also in principle any solvents and diluents which are not hydrogenated or converted in any other way under the hydrogenation conditions.

In a preferred embodiment of the process according to the invention, the hydrogenation is carried out without the addition of a solvent or diluent.

The hydrogenation according to the invention generally results in a mixture which, in addition to cyclododecanone, in some cases comprises at least one by-product and/or at least one unconverted reactant and/or at least one further compound which has been fed to the hydrogenation via, for example, a mixture comprising reactant. The cyclododecanone may be removed from this mixture by at least one suitable method, for example and with preference by at least one distillation.

One advantage of the above-described process according to the invention for preparing cyclododecanone is that cyclododecanone and also cyclododecadienone are obtained in few steps and simultaneously with high selectivity. A further considerable advantage is the fact that the reactant used for the process according to the invention may be dinitrogen monoxide-containing offgases from preferably industrial plants which firstly are available without great cost and secondly enable the integration of the process according to the invention into an existing integrated plant system, allowing the transport path for the reactant to be kept to a minimum, and which also, as potential greenhouse gases, do not have to be fed to a special treatment for disposal, but rather flow directly into a product of value.

The cyclododecanone which is especially preferably obtained in accordance with the invention and has optionally been removed from the product mixture may more preferably, for example, be used to prepare dodecanedicarboxylic acid and/or laurolactam and/or polymers derived therefrom, for example polyamides such as nylon-12 or nylon-6,12.

The present invention is illustrated by the examples which follow.

EXAMPLES

Example 1

Oxidation of cis,trans,trans-1,5,9-cyclododecatriene with $N_2O$

A 250 ml autoclave was initially charged with 92.67 g (0.56 mol) of cis,trans,trans-1,5,9-cyclododecatriene (approx. 98%, commercially available from-DuPont). The autoclave was then sealed and purged with $N_2$. Subsequently, the autoclave was pressurized with $N_2O$ up to 30 bar. The temperature was then increased to 225° C. (maximum pressure during the reaction: 55 bar). After a reaction time of 50 h, the autoclave was cooled and decompressed. The product (96 g) was analyzed by means of quantitative GC and GC-MS. The conversion of cis,trans,trans-1,5,9-cyclododecatriene was 45%. The selectivity for cyclododeca4,8-dienone as an isomer mixture was 92% (molar cis,trans:trans,cis:trans,trans isomer ratios 1:1:0.1). Only small amounts of diketocyclododecenes were formed, of which GC-MS was used to detect a total of five different isomers, and traces of dodeca-4,8,11-trienal (as an isomer mixture).

Example 2

Oxidation of cis,trans,trans-1,5,9-cyclododecatriene with $N_2O$

A 250 ml autoclave was initially charged with 94.30 g (0.57 mol) of cis,trans,trans-1,5,9-cyclododecatriene (approx. 98%, commercially available from DuPont). The autoclave was then sealed and purged with $N_2$. Subsequently, the autoclave was pressurized with $N_2O$ up to 50 bar. The temperature was then increased to 200° C. (maximum pressure during the reaction: 81 bar). After a reaction time of 10 h, the autoclave was cooled and decompressed. The product (102.2 g) was analyzed by means of quantitative GC and GC-MS. The conversion of cis,trans,trans-1,5,9-cyclododecatriene was 35%. The selectivity for cyclododeca-4,8-dienone as an isomer mixture was 92% (molar cis,trans:trans,cis:trans,trans isomer ratios 1:1:0.08). Only small amounts of diketocyclododecenes were formed, of which GC-MS was used to detect a total of five different isomers, and traces of dodeca-4,8,11-trienal (as an isomer mixture).

Example 3

Oxidation of cis,trans,trans-1,5,9-cyclododecatriene with $N_2O$

A 250 ml autoclave was initially charged with 91.5 g (0.56 mol) of cis,trans,trans-1,5,9-cyclododecatriene (approx. 98%, commercially available from DuPont). The autoclave was then sealed and purged with $N_2$. Subsequently, the autoclave was pressurized with $N_2O$ up to 50 bar. The temperature was then increased to 200° C. (maximum pressure during the reaction: 92 bar). After a reaction time of 5 h, the autoclave was cooled and decompressed. The product (99.4 g) was analyzed by means of quantitative GC and GC-MS. The conversion of cis,trans,trans-1,5,9-cyclododecatriene was 30%. The selectivity for cyclododeca-4,8-dienone as an isomer mixture was 95% (molar cis,trans:trans,cis:trans,trans isomer ratios 1:1:0.08). Only small amounts of diketocyclododecenes were formed, of which GC-MS was used to detect a total of five different isomers, and traces of dodeca-4,8,11-trienal (as an isomer mixture).

Example 4

Oxidation of recovered cis,trans,trans-1,5,9-cyclododecatriene with $N_2O$

The effluents from Examples 1 to 3 were collected and distilled under reduced pressure. The first fraction which boiled at 111° C. (20 mbar, $T_{head}$) consisted substantially of cis,trans,trans-1,5,9-cyclododecatriene. The second fraction which boiled at 140° C. (20 mbar, $T_{head}$) consisted substantially of cyclododeca-4,8-dienone. Fraction 1 was oxidized under the conditions of Example 3. Both conversion and selectivity remained unchanged compared to Example 3.

Example 5

Hydrogenation of cyclododeca-4,8-dienone to cyclododecanone 50 g of cyclododeca-4,8-dienone (isomer mixture, fraction 2 from Example 4) and 1 g of Pd/C catalyst (10% by weight of Pd, commercially available from Degussa under the product number E 101 N/D) were introduced into a 100 ml autoclave. 5 bar of hydrogen were injected with stirring. At a reaction temperature of 50° C., further hydrogen was supplied (10 h) until no more hydrogen was absorbed. After cooling, decompressing and filtering off the catalyst, the effluent was analyzed by gas chromatography. The conversion of cyclododeca-4,8-dienone was quantitative. Cyclododecanone was obtained in a substantially quantitative yield (>98%). The only impurities which could be detected by GC-MS were traces of cyclododecane, cyclododecenone and dodecanal.

Example 6

Hydrogenation of cyclododeca-4,8-dienone to cyclododecanone

A 30 ml tubular reactor having liquid circulation was charged with 28 ml of Pd/C catalyst (5% by weight of Pd, commercially available from Degussa under the product number E 101 ND/W). After flushing with nitrogen, a hydrogen pressure of 10 bar was established, the autoclave was heated to 60° C. and 150 ml of methanol (as a startup aid) were pumped into the system by means of a feed pump. The circulation pump was subsequently switched on (circulation: about 100 ml/h) and then the feed was switched to 10 ml/h of cyclododeca-4,8-dienone (trickle mode). After 24 h, the effluent was found to contain, in addition to 1% by weight of methanol, about 98% by weight of cyclododecanone and about 1% of unsaturated compounds. After a further 24 h and a temperature increase to 70° C., 99.5% by weight of cyclododecanone and 0.5% by weight of unsaturated compounds were found.

Subsequently, the plant was modified in such a way that a tubular reactor (postreactor, 10 ml capacity) was additionally installed and was likewise operated at 70° C. In the effluent of the postreactor, no further unsaturated compounds were found and the yield of cyclododecanone was substantially quantitative (>98%).

Example 7

2000 g/h cis,trans,trans-1,5,9-cyclododecatriene and 68 g/h of liquid dinitrogen monoxide are pumped into a turbular reactor (diameter inside 6 mm, length 36 m) via a static mixer. The reactor is heated to 280 ° C. The pressure in the reactor is regulated to 100 bar. After passing through the reaction zone, the reaction mixture is decompressed into two flash containers to 3 bar and subsequently to 600 mbar to separate off $N_2$ formed during the process and unreacted $N_2O$.

The liquid product is subsequently distilled at 60 mbar (seven theoretical separation steps, $T_{bottom}$=170° C., $T_{head}$=130° C.). The product obtained via the head of the distillation column is unreacted cis,trans,trans-1,5,9-cyclododecatriene, which is recycled into the reaction. The product obtained via bottom, which contains mostly cyclododecane-4,8-dienone is distilled in a second column with at least 12 theoretical separation steps at 45 mbar. Cyclododeca-4,8-dienone is distilled off as a mixture of isomers via the head of the column ($T_{bottom}$=193° C., $T_{head}$=160° C.)

On average, 209 g/h cyclododeca-4,8-dienone are obtained. The selectivity of cyclododeca-4,8-dienone is 95% (based on cis,trans,trans-1,5,9-dodecatriene).

We claim:

1. A process for preparing a ketone comprising the reaction of 1,5,9-cyclododecatriene with dinitrogen monoxide to obtain cyclododecadienone.

2. A process as claimed in claim 1, wherein the dinitrogen monoxide source is at least one dinitrogen monoxide-containing offgas of at least one industrial process.

3. A process as claimed in claim 2, wherein the dinitrogen monoxide source is the offgas of an adipic acid plant and/or of a dodecanedioic acid plant and/or of a hydroxylamine plant and/or of a nitric acid plant operated with the offgas of an adipic acid plant and/or of a dodecanedioic acid plant and/or of a hydroxylamine plant.

4. A process as claimed in claim 1, wherein the 1,5,9-cyclododecatriene is reacted with a gas mixture containing from 20 to 99.9% by weight of dinitrogen monoxide, based on the total weight of the gas mixture.

5. A process as claimed in claim 1, wherein the dinitrogen monoxide or the gas mixture containing dinitrogen monoxide is used in liquid form.

6. A process as claimed in claim 1, wherein the reaction is carried out at a temperature in the range from 140 to 350° C. and a pressure in the range from 1 to 1000 bar.

7. A process as claimed in claim 1, wherein the reaction has a conversion of 1,5,9-cyclododecatriene in the range from 1 to 80% at a selectivity based on cyclododecadienone of at least 90%.

8. A process as claimed in claim 1, wherein the 1,5,9-cyclododecatriene is cis,trans,trans-1,5,9-cyclododecatriene and is reacted in (ii) with dinitrogen monoxide to give cyclododeca-4,8-dienone.

9. A process as claimed in claim 1, wherein the cyclododecadienone obtained from the reaction of 1,5,9-cyclododecatriene with dinitrogen monoxide is hydrogenated to obtain cyclododecanone.

10. A process as claimed in claim 9, wherein the hydrogenation is carried out in the presence of a hydrogenation catalyst at a temperature in the range from 0 to 250° C. and a pressure in the range from 1 to 325 bar.

11. A process for preparing cyclododecanone, comprising the steps (I) and (II)

(I) reacting 1,5,9-cyclododecatriene with dinitrogen monoxide to obtain cyclododecadienone;

(II) hydrogenating the cyclododecadienone obtained in (I) to obtain cyclododecanone.

12. A process as claimed in claim 11, wherein the dinitrogen monoxide source used is at least one offgas comprising dinitrogen monoxide from at least one industrial process.

13. A process as claimed in claim 12, wherein the dinitrogen monoxide source is the offgas of an adipic acid plant and/or of a dodecanedioic acid plant and/or of a hydroxylamine plant and/or of a nitric acid plant operated with the offgas of an adipic acid plant and/or of a dodecanedioic acid plant and/or of a hydroxylamine plant.

14. A process as claimed in claim 11, wherein 1,5,9-cyclododecatriene is reacted with a gas mixture containing from 20 to 99.9% by weight of dinitrogen monoxide, based on the total weight of the gas mixture.

15. A process as claimed in claim 11, wherein the dinitrogen monoxide or the gas mixture containing dinitrogen monoxide is used in liquid form.

16. A process as claimed in claim 11, wherein the reaction in (I) is carried out at a temperature m the range from 140 to 350° C. and a pressure in the range from 1 to 1000 bar.

17. A process as claimed in claim 11, wherein the reaction in (I) has a conversion of 1,5,9-cyclododecatriene in the range from 1 to 80% at a selectivity based on cyclododecadienone of at least 90%.

18. A process as claimed in claim 11, wherein the 1,5,9-cyclododecatriene used is cis,trans,trans-1,5,9-cyclododecatriene and is reacted in (I) with dinitrogen monoxide to give cyclododeca-4,8-dienone.

19. A process as claimed in claim 11, wherein the hydrogenation in (II) is carried out in the presence of a heterogeneous hydrogenation catalyst at a temperature in the range from 0 to 250° C. and a pressure in the range from 1 to 325 bar.

20. A process for preparing a ketone comprising the reaction of 1,5,9-cyclododecatriene with dinitrogen monoxide to obtain cyclododecadienone wherein the dinitrogen monoxide source is the offgas of an adipic acid plant and/or of a dodecanedioic acid plant and/or of a hydroxylamine plant and/or of a nitric acid plant operated with the offgas of an adipic acid plant and/or of a dodecanedioic acid plant and/or of a hydroxylamine plant, wherein the dinitrogen monoxide or the gas mixture containing dinitrogen monoxide is used in liquid form, and wherein the 1,5,9-cyclododecatriene is cis,trans,trans-1,5,9-cyclododecatriene and is reacted in (ii) with dinitrogen monoxide to give cyclododeca-4,8-dienone.

* * * * *